United States Patent [19]
Möller et al.

[11] 3,973,555
[45] Aug. 10, 1976

[54] ELECTRODE CELL ASSEMBLY FOR THE CONTINUOUS DETERMINATION OF ION CONCENTRATIONS IN LIVING TISSUES

[76] Inventors: Willi Möller, Gubelstrasse 37, Zurich; Otto Stamm, Dufourstrasse 121, St. Gall, both of Switzerland

[22] Filed: Oct. 15, 1974

[21] Appl. No.: 515,034

[30] Foreign Application Priority Data
Oct. 16, 1973    Switzerland........................ 14659/73

[52] U.S. Cl............................. 128/2 E; 128/2.1 E; 204/195 B; 204/195 G
[51] Int. Cl.²....................... A61B 5/04; B01K 3/06
[58] Field of Search ................. 128/2 E, 2.1 E, 418; 204/195 B, 195 G

[56] References Cited
UNITED STATES PATENTS

| | | |
|---|---|---|
| 2,755,243 | 7/1956 | Beckman et al. ...................... 128/2 E |
| 3,098,813 | 7/1963 | Beebe et al. ................... 128/2.1 E X |
| 3,145,157 | 8/1964 | Arthur et al. .................... 204/195 G |
| 3,224,433 | 12/1965 | Von Dalebor......................... 128/2 E |
| 3,224,436 | 12/1965 | Le Massena ..................... 128/2.1 E |
| 3,415,731 | 12/1968 | Carter............................... 204/195 G |
| 3,458,422 | 7/1969 | Proctor, Jr...................... 204/195 G |
| 3,476,670 | 11/1969 | Weiner............................... 128/2.1 E |
| 3,804,080 | 4/1974 | Ruttgers et al. ................. 128/418 X |
| 3,827,428 | 8/1974 | Hon et al. ........................ 128/418 X |

FOREIGN PATENTS OR APPLICATIONS
259,722   6/1965   Australia............................. 128/2 E

*Primary Examiner*—Kyle L. Howell
*Attorney, Agent, or Firm*—Haseltine, Lake & Waters

[57] ABSTRACT

An electrode cell assembly for the continuous determination of ion concentrations in living tissues, which cell assembly comprises a measuring electrode having an ion selective member, which is shaped in a way so that it can be introduced into the living tissue and which cell assembly, furthermore, has a reference electrode in a housing which is filled with an electrolyte and which housing of the reference electrode has a membrane which is in continuous contact with the surface, e.g., the skin or the tissue of the living being during the determination of the ion concentrations, so that the ion concentration can be continuously read off from a recording device with which the electrode cell assembly is connected.

5 Claims, 2 Drawing Figures

ELECTRODE CELL ASSEMBLY FOR THE CONTINUOUS DETERMINATION OF ION CONCENTRATIONS IN LIVING TISSUES

DESCRIPTION OF THE PRIOR ART

Electrode cell assemblies for the determination of ion concentrations are known in the art and said electrode cell assemblies comprise a measuring electrode, which is immersed into the solution in which the ion concentration shall be determined as well as a reference electrode, which is immersed in an electrolyte solution. the electrical conductivity between the solution in which the ion concentration shall be determined and the electrolyte solution in which the reference electrode is immersed, is generally provided by a bridge solution, i.e., a conduit which is filled with an electrolyte, e.g., the solution into which the reference electrode is immersed, and wherein the end of said conduit is provided with a membrane so that said conduit can be immersed into the solution in which the ion concentration has to be determined, which membrane or diaphragm is an impermeable barrier which prevents the bridge solution (electrolyte solution) from flowing out. The measuring electrode has an ion sensitive member which is immersed into the solution in which the ion concentration shall be determined and said measuring electrode, furthermore, has a buffer solution filling into which the internal reference electrode of said measuring electrode is immersed. The internal reference electrode of the measuring electrode and also the reference electrode are connected with a conductor and the other ends of those conductors are connected via the recording device so that the EMF is recorded by said recording device. The measuring electrode has an ion sensitive member which is immersed into the solution wherein the ion concentration has to be determined and said measuring electrode can, e.g., be one of the well known glass electrodes in which the ion sensitive member is a glass membrane. Electrode cell assemblies in which the measuring electrode is a glass electrode are frequently used for the determination of the pH-value of solutions. We refer to "Lehrbuch der Elektrochemie" von Kortüm, Verlage Chemie, Weinheim Bergstrasse, Edition 1957, pages 292-295.

Furthermore, it is well known in the art to determine the ion concentration in body fluids, e.g., in blood, by using an electrode cell assembly as described above and immersing the measuring electrode into a sample of the body fluid. The ion concentration of said body fluid is then recorded with the calibrated recording device. Said method, for instance, can be applied for the determination of the pH-value of blood samples of a person by taking at certain intervals blood samples from said person and determining the pH-value of said blood samples by using a glass electrode the measuring electrode.

The pH-value of the blood makes it possible to estimate the carbon dioxide concentration in the blood, i.e., if the pH-value of the blood is sinking, this means that the carbon dioxide concentration in the blood is increasing. The increased carbon dioxide concentration in the blood shows that the organs of the living being are not provided with sufficient oxygen and this may be noxious or harmful for the organs, especially for the brain. It would be very advantageous if narcotized persons and persons who are submitted to an intensive medical treatment were continuously observed with regard to the pH-value of their blood so that by such a continuous determination of the pH-value, any increase of the $CO_2$-content in the organism could be noticed immediately. Specially important, however, would be such a continuous investigation if it were possible that during pregnancy any insufficient oxygen supply for the organism of the infant occurs and, furthermore, in the course of a delivery, i.e., during the period of the opening of the cervix and the extrusion of the infant. It is well known that an increase of the carbon dioxide concentration in the blood of the infant, which, e.g., might occur because of a compression of the umbilical cord during the delivery, may cause a permanent damage of the brain of the infant (cerebral palsy). Therefore, it would be very advantageous for the gynecologist if he could observe immediately any increase of the carbon dioxide concentration in the infant organism if any difficulties occur during the pregnancy and in the course of the delivery so that the gynecologist could immediately undertake the necessary steps in order to prevent any harmful influence on the brain of the infant.

Until now, however, a continuous determination of ion concentration in the living organism was not possible but it was necessary to take samples, e.g., blood samples, at certain intervals, e.g., intervals of 20 minutes, and to determine in those samples the ion concentration, e.g., the pH-value. Physicians, in this case however, never knew whether any changes in the organism of the observed person occured during the time before the next sample was taken.

SUMMARY OF THE INVENTION

We now have unexpectedly found that ion concentrations need not be determined in body fluids, like, e.g., blood samples, but that it is also possible to insert the ion sensitive member of the measuring electrode directly into the living tissue so that the concentration of the desired ion can be directly determined in the tissue of the person or living being who is tested. It was found out that an increase of the carbon dioxide concentration in the blood of a living being results within a few minutes in an increase of the carbon dioxide concentration in the tissue of the living being, which increase of the carbon dioxide results in a decrease of the pH-value of the tissue of said living being.

The object of the present invention accordingly is to provide an electrode cell assembly for the determination of ion concentration which makes it possible to measure the ion concentration and changes in the ion concentration in the living tissue during long periods. More specificially an object of the present invention is an electrode cell assembly which is applicable in diagnostic methods and it shall especially be possible to use a preferred electrode cell assembly of said kind for the determination of ion concentrations in the infant organism during the pregnancy and in the first stage and second stage of a delivery.

The object of the present invention, therefore, is an electrode cell assembly for the continous determination of ion concentrations in living tissues, which cell assembly is connected with a recording device and said electrode cell assembly comprises a measuring electrode having an ion selective member as well as a reference electrode, said measuring electrode having its ion selective member in a form which is suited for being introduced into the living tissue and having furthermore, anchoring means for retaining the ion sensitive member in the living tissue and wherein the reference electrode is incorporated into a housing which is filled with an electrolyte, said housing comprising at least one membrane in a position so that during the determination of the ion concentration said membrane is in continuous contact with the surface of the body, preferably the skin, or a tissue of the living being.

According to a preferred embodiment of the cell assembly, said part of the measuring electrode which is suited for being introduced into the living tissue has a conical shape and at least one surface of said conically shaped part or the conically shaped part itself is the ion selective member of said measuring electrode. the conically shaped part of the measuring electrode of this electrode cell assembly then can easily be introduced into the tissue of the living being by penetrating the skin of the living being with the conically shaped part of the measuring electrode and the measuring electrode then is retained in the tissue by the anchoring means during the whole period in which the ion concentration in the tissue is determined. For instance, the anchoring means for anchoring said ion sensitive member of the measuring electrode in the tissue can be a spiral or helix which surrounds said conical part of the measuring electrode. If the measuring electrode is then rotated around the longitudinal axis of said cone, the conical part of the measuring electrode will penetrate the skin and is screwed into the tissue and anchored therein by the spiral. Said spiral prevents any movement of the living being from pushing the ion specific part of the measuring electrode out of the tissue.

The measuring electrode and the reference electrode are united in a single housing to form a single rod electrode cell assembly. This embodiment of the inventive electrode cell assembly is specially suited for certain fields of application, e.g., for the determination of the pH-value in the tissue of the infant during the pregnancy and in the course of a birth.

A further object of the invention is a diagnostic process for the continuous electrometric determination of ion concentrations in living tissues using an electrode cell assembly, which is connected with a recording device, wherein said electrode cell assembly comprises a measuring electrode having an ion sensitive member, which is introduced into the living tissue of the living being and anchored in the living tissue by anchoring means throughout the period in which the ion concentrations are determined continuously. The electrode cell assembly, which is used in this diagnostic process, furthermore, comprises a reference electrode, which is incorporated in a housing which is filled with an electrolyte and said housing comprises at least one membrane which is during the determination of the ion concentrations either in contact with the living tissue or with the surface of the body of the living being.

If, according to said diagnostic process, the ion concentration in a certain tissue of the living being shall be determined, then the person who performs said diagnostic process will penetrate the skin of the living being with the ion sensitive part of the measuring electrode and anchor said part in the tissue. The part of the reference electrode which is provided with the membrane, is either also introduced into the tissue (e.g., by using a single rod cell assembly) or it is brought into permanent contact with the area of the skin of the living being where the ion selective electrode was anchored or with any other part of the skin of the living being. It is then possible to record with the recording device continuously any changes in the concentration of the ion in question. If the membrane of the reference electrode is brought into contact with the skin of the living being, then it is necessary that the contact between the membrane and the skin is very intimate so that the necessary electrical conductivity is provided between the skin and the membrane and thereby with the electrolyte on the other side of the membrane.

A special important diagnostic process for the continuous electrometric determination of ion concentration, in which the inventive electrode cell assembly can be applied is the determination of the ion concentration in the tissue of the unborn child during the pregnancy or the period of the opening of the cervix and the extrusion of the infant in the course of a delivery (first and second stage of the delivery). When the process in question is performed, the single rod cell assembly is introduced through the partially opened cervix and the ion sensitive member of the measuring electrode is introduced and anchored in the living tissue of the infant. The membrane of the housing of the reference electrode is also anchored in the living tissue of the infant.

In all those procedures for determining the ion concentration of the still unborn child or child during the delivery, there can be continuously read off any change of the ion concentration of the tissue of the infant on the recording device, e.g., a decrease of the pH-value which indicates that the oxygen supply to the child is insufficient.

A preferred embodiment of the electrode cell assembly for the determination of ion concentration in living tissue is a cell assembly which is suited for the continuous determination of the pH-value in the living tissue. Electrode cell assemblies for the pH-determination comprise preferably a measuring electrode which is a glass electrode. The ion sensitive member of said glass electrode has preferably the shape of a hollow cone. The tip of said cone as well as the shell of the cone consist of the glass of the ion sensitive glass membrane and said shape is achieved by blowing the glass appropriately. The shell of said hollow cone of this embodiment of the invention is the actual ion sensitive part of the measuring electrode, i.e., the ion sensitive glass membrane. The tip of said cone is not hollow and said tip is used for penetrating the skin of the living being and entering into the tissue so that the ion sensitive part of the measuring electrode, i.e., the shell of said hollow cone is inserted into the living tissue. The glass of said cone, i.e., the glass membrane, is preferably formed of a glass with low electrical resistance and the composition of the glass and the shape (angle of opening) and the size of the tip of the cone which is not hollow, have to be adjusted so that the rigidity of the tip of said cone is sufficient for penetrating the skin of the living being.

If the inventive electrode cell assembly is an assembly for the determination of the pH-value, then, preferably the reference electrode as well as the internal reference electrode of the glass electrode is a silver/silver halide electrode. In order to prevent any poisonous substances from contaminating rooms in which operations are performed if during the handling either the glass electrode or the reference electrode is broken, it is necessary to avoid the use of toxic substances in those electrodes and, therefore, neither the internal reference electrode of the glass electrode nor the reference electrode is a calomel electrode.

For a fuller understanding of the nature and the objects of the present invention, reference should be made to the following detailed description, taken in connection with the accompanying drawing.

Figure 1:
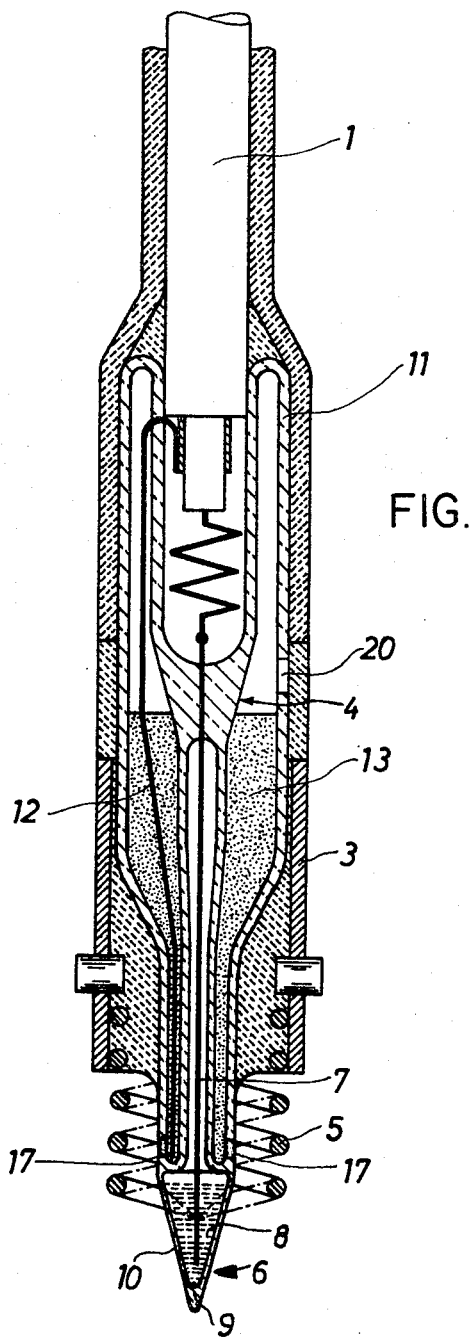
FIG. 1 shows an electrode cell assembly which consists of a single rod electrode, i.e., a measuring electrode and a reference electrode combined in a single electrode body.
Figure 2:
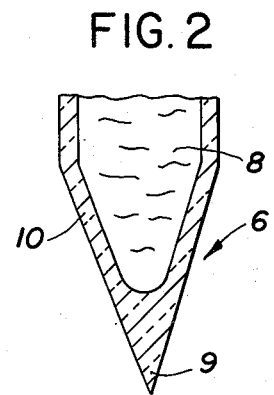
FIG. 2 shows in detail the tip of said measuring electrode, i.e. the part thereof to be inserted into the living tissue.

FIG. 1 shows a longitudinal section of an electrode cell assembly in which the measuring electrode for the determination of the pH-value, i.e., glass electrode 4 and reference electrode 12 are united to form a single electrode body. Around the glass electrode 4 there is arranged the reference electrode 12 so that in the lower part of said electrode cell assembly the end 6 of the glass electrode 4 projects freely. The end 6 of the electrode of the glass electrode has the form of a hollow cone and said end of the electrode is shown enlarged and in detail in FIG. 2. The end of the electrode has a tip 9 and a shell 10 which is made of a glass of low electrical resistance which is suited for the production of membranes of glass electrodes. The hollow part of the hollow cone is filled with a buffer solution 8. An internal reference electrode 7 of the measuring electrode is a silver/silver-chloride electrode which is immersed into the buffer solution 8. To said internal reference electrode 7 of the measuring electrode there is connected electrically conductive cable 1 and the other end of said cable is connected with the recording device which is not shown in the figure.

The housing 11 of the reference electrode 12 surrounds the measuring electrode in such a way that the electrode end of the measuring electrode is projecting free and can be readily inserted into the tissue of the living being by penetrating the skin with said tip 9. In the lowermost part of the housing 11 of the reference electrode 12, there are situated membranes 17 of said reference electrode. The reference electrode is provided with two membranes 17 which are separated from each another and when the end 6 of the measuring electrode is inserted into the living tissue by penetrating the skin, the membranes 17 of the reference electrode also enter into the living tissue so that during the entire period of determination of the ion concentration in the tissue, there is an intimate contact between the living tissue and the membranes 17. By said intimate contact the necessary electrical conductivity is provided.

The conical end 6 of the glass electrode has an upper shoulder and the inner tubular portion of the glass electrode extends axially from said upper shoulder. The reference electrode includes an outer tubular portion merging with housing 11 and extending coaxially around the inner tubular portion and the membranes are mounted in the outer tubular portion adjacent the shoulder of the glass electrode.

The electrolyte solution 13 of the reference electrode 12 is introduced into the housing of the reference electrode through the opening 20. The reference electrode 12 is a silver/silver-chloride electrode which is immersed in the electrolyte solution 13. The silver/silver-chloride electrode is also electrically connected to the cable 1. The housing 11 of the reference electrode 12 is surrounded by stainless steel tube 3 in such a way that not only does the end 6 of the measuring electrode 4 project from tube 3, but the outer tubular portion of the reference electrode which is provided with the membrane 17 also projects from steel tube 3 and accordingly both are ready for being inserted into the living tissue.

A helical or spiral member 5 surrounds reference electrode 12 and is coupled to tube 3 to make it possible to anchor the single rod cell assembly by turning it around its longitudinal axis into the tissue of the living being. Upon turning of the electrode cell assembly around its longitudinal axis the end 6 of the measuring electrode as well as the member 5 penetrate the skin of the living being and proceed into the tissue and the member 5 is screwed into the tissue and is maintained therein during the entire period of the determination of the ion concentration. After said determination is finished, it is only necessary to turn the electrode cell assembly around its longitudinal axis in a direction opposite the direction in which the member 5 was screwed in, so that the member 5 and the end of the measuring electrode are screwed out of the tissue and can be separated from the living being in which said measuring electrode had been anchored throughout the determination.

What is claimed is:

1. An electrode cell assembly for the continuous determination of ion concentration in living tissues, said assembly comprising a measuring electrode including a hollow glass electrode, a steel tube surrounding said electrode, said electrode having a conical end projecting freely from said steel tube, said conical end being of low electrical resistance and constituted as an ion sensitive membrane, an internal reference electrode mounted axially in said glass electrode, a buffer solution in said hollow glass electrode, said reference electrode being immersed in said buffer solution, a housing surrounding said glass electrode and integrated therewith to define an annular chamber, an electrolyte in said annular chamber, a reference electrode in said annular chamber and inserted into said electrolyte, said housing merging with said conical end of the hollow glass electrode, membrane means supported by said housing in the region where the latter merges with the conical end of the glass electrode for contact with the living tissue when the conical end is brought into operative association with the living tissue, and anchoring means coupled to said steel tube and surrounding said reference electrode for retaining the measuring electrode in operative association with the living tissue.

2. An electrode cell assembly as claimed in claim 1, wherein said anchoring means comprises a sprial member.

3. An electrode cell assembly as claimed in claim 1, wherein said internal reference electrode is a silver/silver chloride-electrode and said reference electrode is also a silver/silver chloride-electrode.

4. An electrode cell assembly as claimed in claim 1, wherein said membrane means comprises a pair of opposed membrane members mounted in said housing immediately proximate the said conical end of the glass electrode.

5. An electrode cell assembly as claimed in claim 4 wherein said conical end of the glass electrode has an upper shoulder, said glass electrode including an inner tubular portion extending axially from said upper shoulder, said reference electrode including an outer tubular portion extending coaxially around said inner tubular portion, said opposed membrane members being mounted in said outer tubular portion adjacent said shoulder of the glass electrode.

* * * * *